US011116890B2

(12) United States Patent
Röhl (10) Patent No.: US 11,116,890 B2
(45) Date of Patent: Sep. 14, 2021

(54) OCULAR WORK TIP SLEEVE ADAPTER

(71) Applicant: SURGICAL DESIGN CORPORATION, Armonk, NY (US)

(72) Inventor: Rainer Röhl, Simmerath (DE)

(73) Assignee: SURGICAL DESIGN CORPORATION, Armonk, NY (US)

( * ) Notice: Subject to any disclaimer, the term of this patent is extended or adjusted under 35 U.S.C. 154(b) by 171 days.

(21) Appl. No.: 15/687,734

(22) Filed: Aug. 28, 2017

(65) Prior Publication Data

US 2019/0060555 A1    Feb. 28, 2019

(51) Int. Cl.
| | | |
|---|---|---|
| *A61M 3/02* | (2006.01) | |
| *A61F 9/007* | (2006.01) | |
| *A61M 1/00* | (2006.01) | |

(52) U.S. Cl.
CPC ....... *A61M 3/0283* (2013.01); *A61F 9/00745* (2013.01); *A61M 1/742* (2021.05); *A61M 1/7411* (2021.05); *A61M 1/774* (2021.05); *A61M 1/84* (2021.05); *A61M 1/85* (2021.05); *A61M 2210/0612* (2013.01)

(58) Field of Classification Search
CPC .. A61M 3/0283; A61M 1/0033; A61M 1/008; A61M 2210/0612; A61M 1/0058; A61M 1/0031; A61M 1/741; A61M 1/742; A61F 9/00745; A61F 9/00736; A61F 9/008; A61F 9/007; A61B 17/32002; A61B 17/320068
USPC ..................................................... 604/22, 33
See application file for complete search history.

(56) References Cited

U.S. PATENT DOCUMENTS

| | | | | |
|---|---|---|---|---|
| 3,088,323 A * | 5/1963 | Welkowitz | ............ | G01L 9/0052 |
| | | | | 73/727 |
| 3,618,611 A * | 11/1971 | Urban | .............. | A61B 17/32002 |
| | | | | 606/170 |
| 3,710,781 A * | 1/1973 | Huthcins, IV | .... | A61M 25/0069 |
| | | | | 600/488 |
| 3,776,238 A * | 12/1973 | Peyman | .............. | A61F 9/00763 |
| | | | | 606/171 |
| 3,815,604 A * | 6/1974 | O'Malley | .......... | A61B 18/1206 |
| | | | | 604/22 |
| 3,937,222 A * | 2/1976 | Banko | ................. | A61F 9/00763 |
| | | | | 606/170 |
| 4,011,869 A * | 3/1977 | Seiler, Jr. | ............ | A61F 9/00763 |
| | | | | 604/22 |

(Continued)

*Primary Examiner* — Nathan R Price
*Assistant Examiner* — Mark A Igel
(74) *Attorney, Agent, or Firm* — Leason Ellis LLP (57) ABSTRACT

An adapter for a surgical hand piece having a single lumen work tip with an open end and a small lateral hole is designed to convert the work tip to infusion/aspiration (I/A) cleanup of lens epithelial cells after phacoemulsification. The adapter is in the form of a sleeve adapted to be slid over the distal end of the work tip. The sleeve includes at least one aspiration hole located toward the distal end of the sleeve. When the distal end of the sleeve is at a first distance $L_1$ from the distal end of the work tip, aspiration occurs through the aspiration hole of the sleeve and the open end of the work tip. When the distal end of the sleeve is at a second and smaller distance $L_2$ from the open end of the work tip, aspiration through the open end of the work tip is blocked by the sleeve and aspiration occurs through the aspiration hole of the sleeve and the lateral hole in the work tip.

12 Claims, 4 Drawing Sheets

(56) References Cited

U.S. PATENT DOCUMENTS

| | | | | |
|---|---|---|---|---|
| 4,014,333 A * | 3/1977 | McIntyre | A61F 9/00736 | 604/43 |
| 4,099,529 A * | 7/1978 | Peyman | A61F 9/00763 | 30/241 |
| 4,111,207 A * | 9/1978 | Seiler, Jr. | A61F 9/00763 | 30/241 |
| 4,504,264 A * | 3/1985 | Kelman | A61F 9/00745 | 604/22 |
| 4,513,745 A * | 4/1985 | Amoils | A61F 9/00763 | 604/22 |
| 4,548,205 A * | 10/1985 | Armeniades | A61F 9/00736 | 600/561 |
| 4,643,717 A * | 2/1987 | Cook | A61F 9/00745 | 604/22 |
| 4,678,459 A * | 7/1987 | Onik | A61B 17/32002 | 604/22 |
| 4,722,350 A * | 2/1988 | Armeniades | A61B 3/16 | 600/561 |
| 4,819,635 A * | 4/1989 | Shapiro | A61F 9/00763 | 600/565 |
| 4,850,354 A * | 7/1989 | McGurk-Burleson | A61B 17/32002 | 606/170 |
| 5,056,902 A * | 10/1991 | Chinnock | A61B 34/73 | 359/503 |
| 5,059,204 A * | 10/1991 | Lawson | B25D 11/102 | 606/171 |
| 5,242,385 A * | 9/1993 | Strukel | B06B 1/085 | 604/22 |
| 5,267,996 A * | 12/1993 | Fletcher | A61B 5/0084 | 604/35 |
| 5,282,786 A * | 2/1994 | Ureche | A61M 3/0279 | 604/22 |
| 5,285,795 A * | 2/1994 | Ryan | A61B 17/32002 | 600/562 |
| 5,358,473 A * | 10/1994 | Mitchell | A61F 9/00736 | 604/27 |
| 5,464,389 A * | 11/1995 | Stahl | A61F 9/00745 | 604/22 |
| 5,718,677 A * | 2/1998 | Capetan | A61M 1/84 | 604/35 |
| 5,766,194 A * | 6/1998 | Smith | A61B 17/3203 | 606/1 |
| 5,782,849 A * | 7/1998 | Miller | A61B 17/32002 | 606/159 |
| 6,068,477 A * | 5/2000 | Mahlmann | A61C 17/08 | 433/96 |
| 6,579,270 B2 * | 6/2003 | Sussman | A61F 9/00736 | 604/264 |
| 6,902,558 B2 * | 6/2005 | Laks | A61F 9/00709 | 604/35 |
| 7,083,589 B2 * | 8/2006 | Banko | A61F 9/00745 | 433/119 |
| 7,276,060 B2 * | 10/2007 | Madden | A61F 9/00736 | 606/27 |
| 7,329,261 B2 * | 2/2008 | Perkins | A61F 9/00745 | 606/107 |
| 8,282,574 B2 * | 10/2012 | Coonahan | A61B 10/0275 | 600/564 |
| 8,282,594 B2 * | 10/2012 | Perkins | A61M 3/0279 | 604/22 |
| 8,313,501 B2 * | 11/2012 | Miller | A61B 17/32 | 606/171 |
| 8,403,951 B2 * | 3/2013 | Chon | A61F 9/00745 | 606/171 |
| 8,641,658 B1 * | 2/2014 | Banko | A61F 9/00745 | 604/22 |
| 8,657,840 B2 * | 2/2014 | Palmer | A61B 17/32002 | 606/170 |
| 8,721,581 B2 * | 5/2014 | Zolli | A61F 9/00736 | 604/19 |
| 10,166,317 B2 * | 1/2019 | Banko | A61F 9/00745 | |
| 10,179,068 B2 * | 1/2019 | Banko | A61M 1/774 | |
| 2005/0234473 A1 * | 10/2005 | Zacharias | A61F 9/00745 | 606/107 |
| 2005/0256462 A1 * | 11/2005 | Underwood | A61F 9/00736 | 604/264 |
| 2008/0167604 A1 * | 7/2008 | Hong | A61M 1/85 | 604/27 |
| 2012/0157934 A1 * | 6/2012 | Liao | A61F 9/00745 | 604/264 |
| 2013/0231605 A1 * | 9/2013 | Walter | A61F 9/00745 | 604/22 |
| 2014/0276377 A1 * | 9/2014 | Chang | A61M 1/85 | 604/35 |
| 2015/0005753 A1 * | 1/2015 | Walter | A61F 9/00745 | 606/6 |
| 2015/0025451 A1 * | 1/2015 | Banko | A61F 9/00745 | 604/35 |

* cited by examiner

Fig. 8

OCULAR WORK TIP SLEEVE ADAPTER

TECHNICAL FIELD

The present invention is generally directed to hand pieces for ocular surgery, particularly for the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

Figure 1:
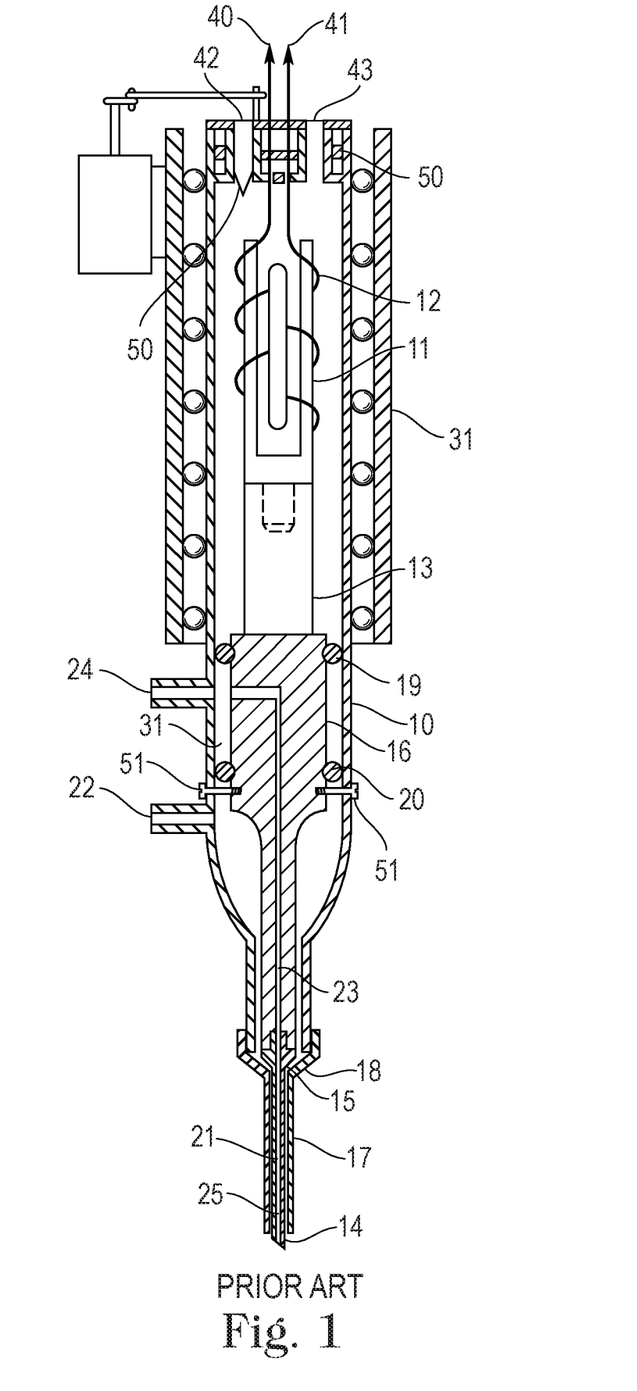
FIG. 1 is a view in cross-section of a prior art type of surgical hand piece.

FIG. 1 depicts one such type of prior art ultrasonic hand piece as shown in U.S. Pat. No. 4,504,264 of Kelman. This hand piece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is connected, such as by a screw thread, to the narrowed distal end of the connecting body 16 so as to be coupled to the transducer 11. As a result, the work tip is longitudinally vibrated by the transducer. The working tip 14 is an elongated, hollow tip of a suitable metal, such as titanium, that is capable of supporting ultrasonic vibrations. It has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tip 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric 0-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between 0-ring 19 and a grommet 50 for circulation around the transducer. This is not always necessary and is not used in most present day hand pieces.

The sleeve 17 around the tip 14 forms a first fluid passage 21 between the tip 14 and the sleeve for an infusion/irrigation fluid. An inlet 22 is provided on the housing or sleeve distally of the 0-ring 20 for supplying the irrigation fluid to the passage 21 from a fluid supply, e.g., a bag of saline solution (not shown).

A passage 23 is formed through the connecting body 16 that is in communication with a central passage 25 of the work tip 14. An outlet 24 on the housing or sleeve receives a suction (aspiration) force that is applied to the passage 23 in the connecting body and the central passage 25 in the work tip. A chamber 31 is formed between the spaced 0-rings 19, 20 on the body 16 and the housing 10, with which the aspiration force from outlet 24 communicates. Thus the aspiration force is from the source (e.g., a suction pump not shown), into the chamber 31 between the 0-rings, through the passage 23 in the connecting body and the passage 25 in the work tip 14. Tissue that is emulsified by the work tip is aspirated from the operating site by the aspiration flow force. In particular, saline solution introduced into the eye through fluid passage 21 and tissue displaced by the vibration force of the tip 14, is drawn into the distal end of passage 25 and passes out of the hand piece through outlet 24. It should be noted that passage 25 is located concentrically within passage 21.

As indicated, other apparatus (not shown) for use with the hand piece include the suction pump for producing the aspiration fluid (suction), the treatment fluid supply (infusion/irrigation fluid, such as a saline liquid), an oscillator for applying an electrical signal to the vibratory structure and control apparatus therefore. All of these are of conventional construction.

Considering now the operation of the hand piece of FIG. 1. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip 14. Treatment fluid is supplied through inlet 22 and fluid passage 21 to bathe the tissue in the operating site region around the working tip 14. Suction force is applied through inlet 24 and passage 23 to the working tip 14 passage 25 to withdraw the tissue fragmented by the work tip along with some of the treatment fluid.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag of the eye and to remove them. Doing this procedure provides a more stable and long-term fixation for certain types of IOL's in the capsular bag. One manner of accomplishing the cleanup is to use a combination of low force irrigation of the capsular bag interior with a liquid together with the application of low power ultrasonic energy. This dislodges the unwanted cells and substances without damage to the capsular bag. Further, this material can be removed from the capsular bag by the aspiration fluid flow, which also may be reduced in pressure to avoid damage.

Figure 2:
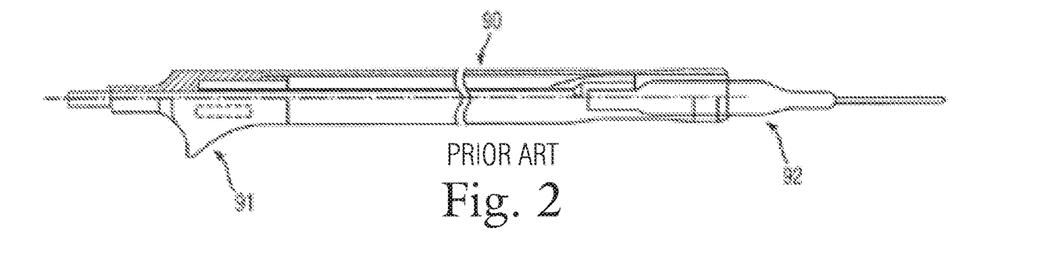
FIG. 2. is a partial crosssectional view of a prior art irrigation/aspiration instrument with a removable tip.
Figure 3:
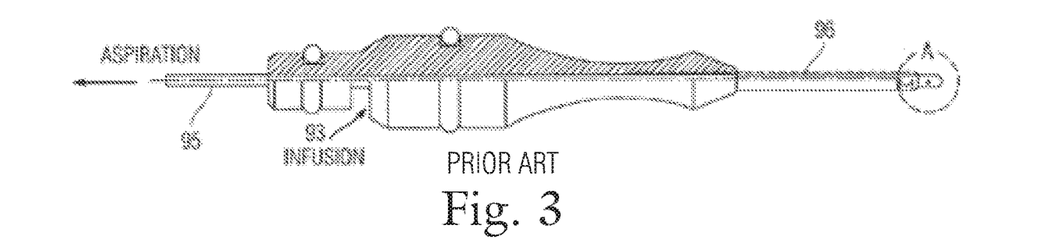
FIG. 3 is a partial cross-sectional enlarged view of the prior art tip for the infusion/aspiration instrument of FIG. 2.

In a cleanup procedure it is advantageous if the flow of the irrigation liquid can be made more directional than would be possible using the hand piece with the outer sleeve through which the liquid flows and exits from around the work tip that produces the ultrasonic energy. It is also better if the aspiration force is lower. As a result, typically a different tip from the one illustrated in FIG. 1, which breaks up the tissue, is used for the cleanup. In fact a completely different instrument called an irrigation or infusion/aspiration (I/A)

instrument is often used for this purpose. Such an instrument 90 is illustrated in FIG. 2. It has a handle 91 at one end and a work tip 92 at the other end. An enlarged view of the work tip is shown in FIG. 3. The I/A instrument work tip has concentric infusion and aspiration lumens, and typically has no ultrasonic vibration capability. The infusion fluid enters the work tip at opening 93 and is in an outer concentric lumen so that its flow surrounds the distal part of lumen 95 of the work tip. The aspirated tissue enters a small hole 94 in the distal part and is withdrawn through lumen 95. Thus, when the phacoemulsification has been completed and cleanup is to be started, the surgeon must remove the phacoemulsification tool from the eye. Then the surgeon removes the first or phacoemulsification work tip, replaces it with a different cleanup work tip and then inserts the new work tip or a separate I/A tool 90 is inserted in to the eye. This second insertion into the eye increases the possibilities of infection and trauma. Also, the I/A tool has a disadvantage in that the surgeon would have to keep inserting and withdrawing the ultrasonic work tip and the I/A tool from the eye as the process is completed, because the surgeon cannot be sure that all of the tissue has be broken up until the cleanup process has begun. As a result, this would also subject the patient to the increased possibilities of infection and trauma.

Figure 4:
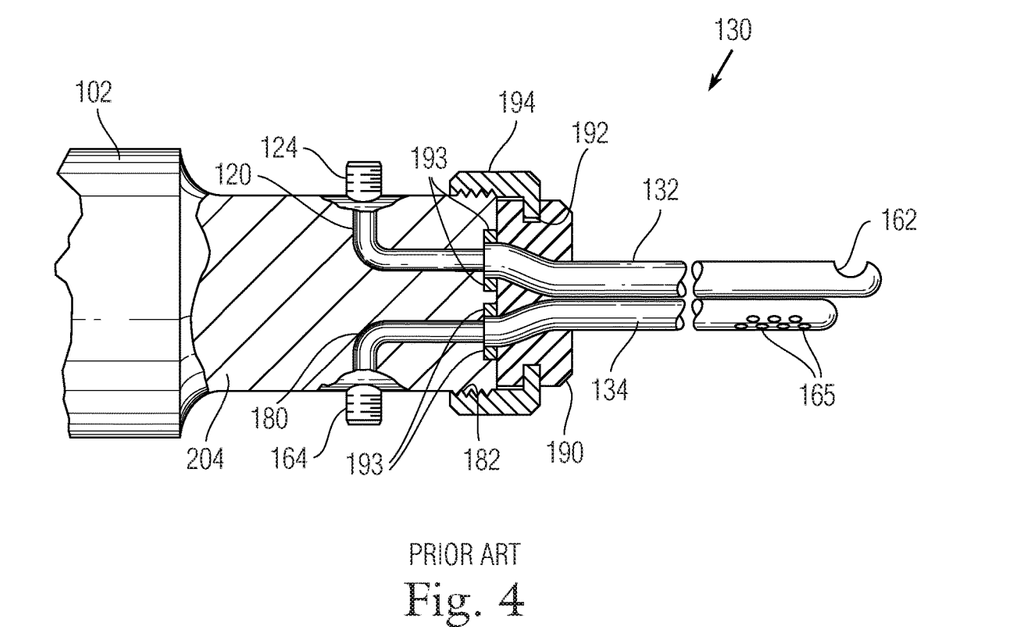
FIG. 4 is a cross-sectional view of a prior art dual lumen surgical hand piece.

As shown in U.S. Pat. No. 8,641,658, the surgical instrument may be provided with dual lumens in tubes 132, 134, each of which can alternatively be used for aspiration of emulsified tissue and irrigation of the surgical site. FIG. 4 shows a work tip 130 that can be connected to an ultrasonic energy source 102 of a hand piece by means of a connecting body 204. Two fluid passages 120 and 180 for aspiration or irrigation fluid pass through the connecting body 204. For example the proximal end of passage 120 can be in communication with the irrigation fluid input of the supply line 124 and the proximal end of passage 180 can be in communication with the aspiration fluid of the supply line 164. The distal ends of the two passages 120 and 180 terminate at the distal end of the connecting body 204.

There are threads 182 around the connecting body distal end. A hub 190 is around the proximal ends of the work tip tubes 132 and 134, which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 aligned with the distal end of passage 180.

When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. O-rings 193 are provided in the connecting body at the distal ends of passages 120 and 180 to make the communications fluid tight.

Both of the tubes 132 and 134 receive the ultrasonic energy from the source 102 (not shown). A valve (not shown) can be used with the hand piece of FIG. 4 to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

The work tip can be used with only an irrigation/aspiration (I/A) function by turning off the source of ultrasonic energy and only supplying the aspiration and irrigation fluids. Thus, the same instrument can be used for the phacoemulsification function while performing irrigation and aspiration as an operation takes place and also only for I/A functions (no or minimal ultrasonic energy is used) useful for cleaning the capsular bag as described above. This eliminates the need for the surgeon changing instruments and also provides the surgeon with a work tip having two tubes with different shape openings available for both aspiration and irrigation.

Only one of the tubes, e.g., 134, can be used as an I/A work tip. In the oval shaped openings 165 along the tube length can be used alone in the eye capsular bag for the substance and cell cleanup procedure described above. The oval shaped openings 165 allow for both good dispersion of the irrigation fluid or a large area for aspiration of cells and substances dislodged by the irrigation liquid.

While the work tip of U.S. Pat. No. 8,641,658 can use its dual lumen tubes for phacoemulsification and for I/A cleanup thereafter, it would be advantageous if these functions could be provided to a single axial work tip as shown in FIG. 1. In addition, it would be beneficial if phacoemulsification instruments with single lumens could have their operation varied without withdrawing the instrument from the eye and/or diverting the surgeon's attention from the operating site. This would reduce the chances of infection and trauma.

SUMMARY OF THE INVENTION

In accordance with the invention a surgical hand piece is provided that can perform all of the functions of emulsification of tissue and other substances by ultrasonic energy and aspiration of such tissue and substances, as well as reduced pressure irrigation and aspiration of a site that is being worked on in order to clean up the site. The hand piece can be used for surgery on appropriate tissue throughout the body, e.g., neurological tissue and ocular tissue.

The invention provides a surgical phacoemulsification hand piece that has a single axial work tip that is concentric to a surrounding irrigation tube. Thus it can be like the prior art work tip in FIG. 1 or an improved work tip as shown in U.S. Patent Application Publication No. US 2015/0025451 A1, which is incorporated herein by reference in its entirety. The improved design has a disposable work tip so that the entire handpiece need not be sterilized between operations.

During a phacoemulsification procedure, an ultrasonic source in the hand piece causes the single work tip to vibrate and to remove cataract tissue. However, when this is complete, the ultrasonic vibration is ended and an adapter converts the work tip for I/A so that it is adapted to clean up of the capsular bag by changing the configuration of the aspiration opening.

In one embodiment the work tip is removed from the eye and an adapter is placed over it so as to modify the opening. In a second embodiment the adapter is fixed to the work tip and its configuration is changed when I/A clean up is desired. With the second embodiment the adapter can be changed without removing the work tip from the eye. For example, the surgeon can pull or push on the proximal end of the adapter that sticks out of the surgical site. Also, the surgeon can selected one of a variety of adapters such that the aspiration pattern during the cleanup can be selected to suit the circumstances. These different patterns can be achieved without the surgeon having to remove the I/A tool from the eye.

The principles of the invention have numerous advantages. For example, the invention allows a phacoemulsification tool to be converted with an adapter to serve as an I/A clean up tool. Further, an embodiment of the invention allows for the elimination of the need for the surgeon to remove an ultrasonically-driven work tip from the operating site, such as the eye, and to insert a separate work tip or tips having 1/A cleanup capability, in order to perform special procedures, such as cortical and lens epithelial cell cleanup. Further, if an I/A tool is used according to the present invention, clean up can be commenced without the surgeon having to divert his attention from the eye.

BRIEF DESCRIPTION OF THE DRAWINGS

The foregoing and other objects and advantages of the present invention will become more apparent when considered in connection with the following detailed description and appended drawings in which like designations denote like elements in the various views, and wherein.

DETAILED DESCRIPTION OF THE INVENTION

Figure 5:
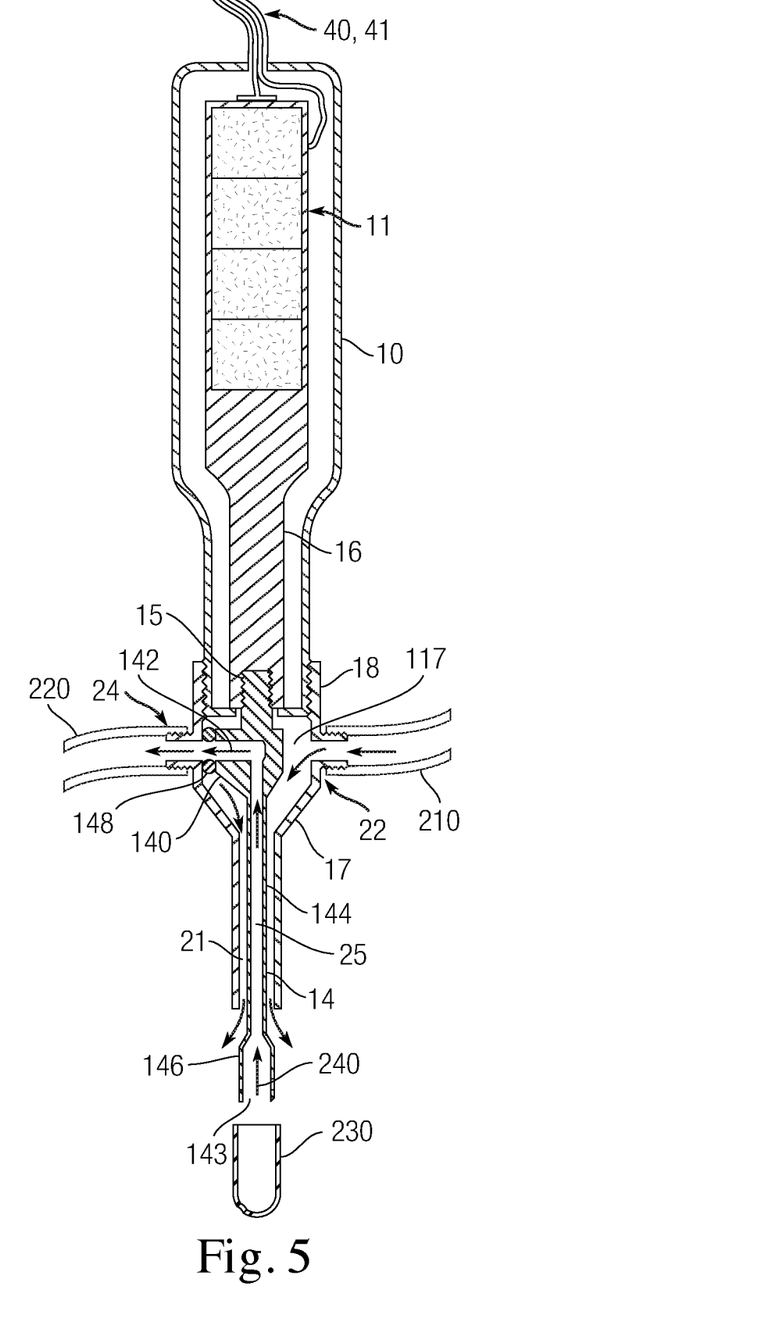
FIG. 5 is an embodiment of a surgical hand piece with a single axial work tip and an adapter for I/A clean up of a capsular bag of the eye according to the present invention.

FIG. 5A shows an embodiment of a handpiece disclosed in US Patent Application Publication US 2015/0025451 A1, which is incorporated herein by reference in its entirety. This handpiece is shown receiving an adapter 230 according to the present invention. The handpiece uses a number of the components of the prior art type of handpiece described above with respect to FIG. 1. The source of the electromechanical energy is shown schematically as transducer 11. This transducer can be either the electromagnetic type or the piezoelectric crystal type. It is preferred, and is conventional, that the output power of the transducer 11 be controlled by electrical signals delivered over wires 40, 41 from a control unit (not shown). These signals allow the ultrasonic power at the work tip distal end 146 to be varied as needed by the surgeon.

Connected to the transducer 11 is the connecting body 16. Both the transducer 11 and connecting body 16 are provided in a housing 10. Although not shown for the sake of clarity, the transducer and connecting body are suspended within housing 10 so as to permit the longitudinal vibration of the transducer and connecting body to occur relative to the housing. For example, the 0-rings 19 and 20 shown in FIG. 1 are spaced apart around the connecting body 16 and engage the inner surface of the housing 10.

The work tip 14 has an opening 143 that leads to an axial channel 25 extending from the opening to an enlarged hub 140 at the proximal end of the work tip. Within the hub 140 there is a radial channel 142 that extends from the axial channel 25 to the outer surface of the hub. While the radial channel 142 is shown at a right angle to the axial channel, in fact it can be at any convenient angle that allows it to extend from the axial channel to the outer surface of the hub. A threaded connector 15 extends from the proximal end of the hub and engages the distal end of the connecting body 16.

A sleeve 17, which may advantageously be made of silicone, is provided with a funnel shape so that its proximal end 18 is large enough to encompass the enlarged hub, and still leave space for chamber 117 between the outer surface of the hub and the inner surface of the sleeve. The distal end of the sleeve tapers down around the portion 144 of the work tip beyond the hub, which extends to a flared portion 146 of the work tip which is at the operating or distal end. As a result the axial channel has a larger diameter at the distal end that tapers down to a smaller diameter as it extends through the work tip into the hub 140. The sleeve stops short of the portion 146. The proximal end 18 of sleeve 17 makes a threaded connection with the body 10. Although not shown, a sterile sheet may be fastened to the end 18 and draped over the housing to avoid contaminating the housing during procedures.

Sleeve 17 has a first external connector 22 on its outer surface that is in fluid communication with the chamber 117. A tube 210 carrying irrigation fluid may be connected to connector 22 in order to supply irrigation fluid to chamber 117. Fluid in chamber 117 may flow between the outer surface of work tip portion 144 and the inner surface of sleeve 17 in a channel 21 so as to exit the handpiece just short of the flared portion 146 of the work tip, i.e., at the site of the operation of the handpiece on the patient's tissue. Sleeve 17 also has a second external connector 24 on its outer surface. In the drawing this connector is shown as being on the opposite side of the sleeve from the connector 22. However, in practice this connector can be at any convenient location on the sleeve. A seal piece 148, e.g., an O-ring or other form of seal, connects the radial channel 142 to the second connector 24. A tube 220 provides a suction force (e.g., from a peristaltic aspiration pump) on connector 24. This causes tissue to be drawn into the opening at portion 146 of the work tip, to travel up the axial channel 25 and into the radial channel 142, to pass through the O-ring 148 and the connector 24, and finally to be drawn through tube 220 to the aspiration pump.

In operation the handpiece of FIG. 5 operates similar to other phacoemulsification handpieces. Electrical energy is applied through wires 40, 41, which causes the ultrasonic transducer to vibrate axially at ultrasonic frequencies. The mechanical axial force is transmitted to the connecting body 16, which in turn transmits it to the work tip 14. When the end 146 of the work tip is placed in contact with tissue, e.g., a cataract, the vibration causes the tissue to break up. While this is occurring, irrigation fluid, e.g., saline solution, passes from a source, through tube 210 and connector 22 into chamber 117, along channel 21 and is deposited at the operating site as shown by the arrows in FIG. 5. At the same time the fragmented tissue is drawn into the opening 143 in portion 146 as shown by arrow 240 in FIG. 5. It passes up the axial channel 25 into the radial channel 142, through the O-ring 148 and connector 24 to tube 220.

The work tip of the present invention can be used with only an infusion/aspiration (I/A) function. That is, the source of ultrasonic energy can be turned off or reduced. The aspiration and infusion/irrigation fluids are supplied to the tubes 210 and 220; but, the aspiration force can be lowered, e.g., from 500 mm Hg to 5-10 mm Hg during the cleaning operation so that the posterior capsule tissue at the back of the eye is not drawn into the tube. The irrigation fluid force can also be lowered. However, it is preferable to utilize smaller openings than that of the work tip at 146. One way to accomplish this is to withdraw the work tip from the eye of the patient and to place an adapter 230 over the end of the work tip.

Figures 6A, 6B:
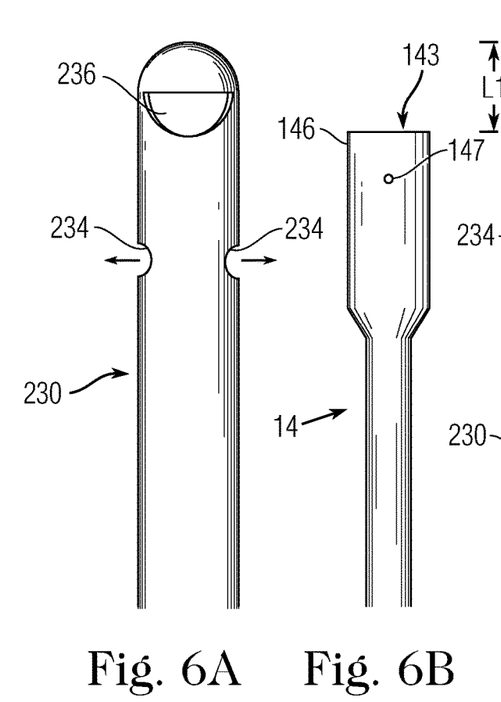
FIG. 6A is an enlarged view of an I/A clean up adapter according to the present invention and FIG. 6B is a work tip on which the adapter can be used.

The adapter 230 as best shown in FIG. 6A is a tube with small lateral openings 234 which allow irrigation fluid to reach the operating site. In addition a larger opening 236 is provided at the distal end of the tube. Opening 236 can have a variety of shapes with a half-moon shape being shown in FIG. 6A. Opening 236 is used for aspiration, so its size and shape depend upon the type of aspiration being performed.

Figures 7A, 7B:
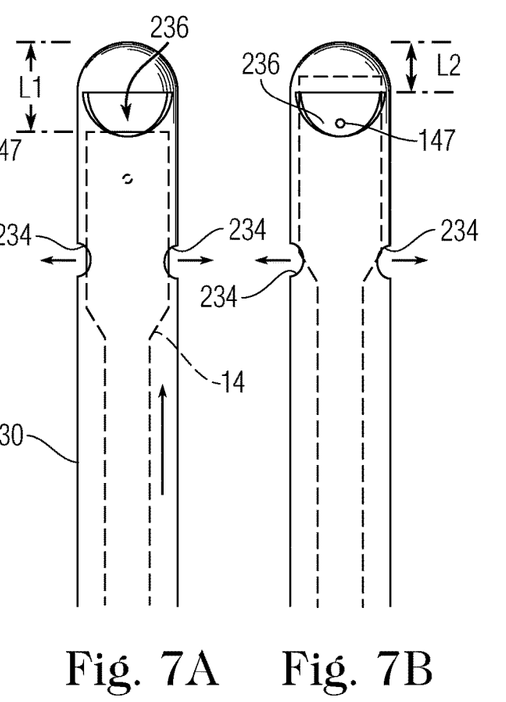
FIG. 7A is an enlarged view of the I/A clean up adapter of FIG. 6A with the work tip of FIG. 6B shown in dotted line within the adapter in a first position and FIG. 7B shows the work tip within the adapter in a second position.

A phacoemulsification work tip 14 with expanded or flared portion 146 is shown in FIG. 6B. This work tip is modified from a conventional work tip in that it includes a lateral hole 147. As shown in FIG. 7A, the adapter 230 can be located over work tip 14 and positioned so that the distal end of the work tip is at a distance $L_1$ from the distal end of the adapter 230. In this position normal phacoemulsification can be performed. In particular, irrigation fluid is directed to the surgical site through lateral openings 234. Tissue is aspirated through opening 236 in the adapter 230. This tissue enters the open end 143 of flared part 146 of the work tip.

During clean up the adapter is withdrawn so that it is positioned such that the distal end of the work tip is at a distance $L_2$, smaller than $L_1$, from the distal end of the adapter 230. In this position, the open end 143 of the flared part 146 of the work tip is blocked by the closed distal end of the adapter. The small hole 147 in the flared part is now centered in the opening 236 so that the aspiration force is limited by the size of the hole 147 and is greatly reduced. Thus, the remaining tissue (i.e., lens epithelial cells) is aspirated through this small hole while irrigation fluid continues to be applied to the site from openings 234. The adapter can be made of metal or soft plastic. If it is made of metal, a soft plastic coating is preferred to avoid damage to the capsular bag of the eye.

When the adapter is slid onto the flared part 146 of the work tip it can be held there do to the suction force of aspirations. As an alternative it may be provided with a slot on its inner surface that engages protrusions on the outer surface of the work tip (not shown).

With the designs of FIGS. 6 and 7, it may be convenient for the surgeon to remove the work tip from the eye of the patient in order to adjust the position of the particular adapter. This of course takes time away from the procedure, exposes the surgical site to infection and/or trauma. Thus, it would be advantageous to be able to change the relative position of the adapter without having to remove the work tip form the eye. In one embodiment the surgeon can simply pull or push on the proximal end of the adapter that sticks out of the surgical site.

Figure 8:
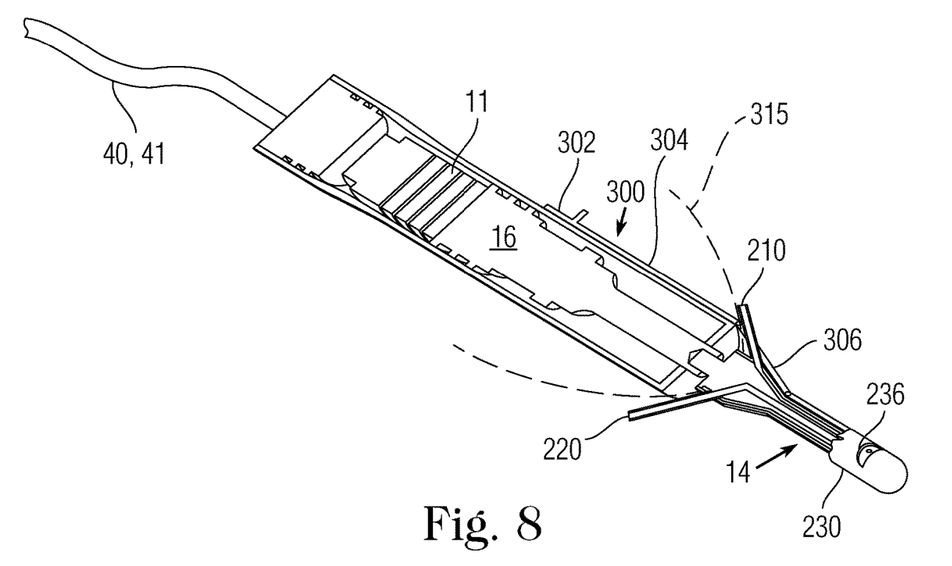
FIG. 8 is a perspective view of a hand piece with a mechanism for sliding a sleeve to change the function of an adapter according to the present invention without removing the work tip from the eye of the patient.

FIG. 8 shows a hand piece with a work tip 14 at the end. Either the irrigation sleeve 17 or an additional sleeve 230 located outside the irrigation sleeve can slide along the work tip. In the embodiment of FIG. 8, the sliding of the sleeve 230 is achieved with a mechanism 300 attached to the exterior of the hand piece, as disclosed in the applicant's copending application Ser. No. 15/687,762, which is incorporated herein by reference. Mechanism 300 includes a thumb portion 302. The thumb portion is connected to a linear portion 304 that runs along the exterior surface of the hand piece and is slidable with respect to that surface. A slanted portion 306 extends from the linear portion down to the work tip and then connects to sleeve 320. All of the portions of mechanism 300 are slidable with respect to the hand piece. The mechanism 300 is preferable located on the hand piece such that it does not interfere with the irrigation and aspiration tubes and is close to the body of the hand piece. Also, preferably, the pieces 302, 304, 306 and 230 are flexibly joined to each other so that during the sliding motion, they do not extend way from the body of the work piece. Depending on the shape of the hand piece, additional or fewer sections of the mechanism 300 may be used. Also, a sterile sheet 315 is shown attached to the hub of the work tip. A portion or portions of the mechanism would penetrate the sterile sheet, if used, to reach the thumb portion 302 on the housing.

When the surgeon completes the emulsification of the cataract and wants to start clean up the remaining tissue, he or she turns off the ultrasonic energy or reduces it, reduces the force of the irrigation and aspiration fluid flows and uses his or her thumb to slide the sleeve 320 forward. This can all be accomplished without removing the work tip from the surgical site within the patient's eye. In general the effect of sliding the adapter is to cause to openings in the work tip to be reconfigured for I/A clean up.

While the invention has been shown and described in connection with the removal of a cataract from the eye of a patient and subsequent I/A clean up, the apparatus and method may also be used for other types of surgery in other parts of the body, e.g., the removal of neurological tissue. If the other tube, e.g. 132, is used, its opening 162 (generally used for aspiration during phacoemulsification) can be used for cleanup.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. An adapter for a surgical hand piece having a single lumen work tip extending from a housing and having an open end and a lateral hole through the work tip with a diameter smaller than the diameter of the open end and located at a distance in the proximal direction from the open end, said work tip being adapted to be ultrasonically vibrated, said adapter being designed to convert the work tip from performing phacoemulsification in which a sharp end of the work tip is ultrasonically vibrated in contact with tissue causing pieces to break off and be aspirated through the open end, to performing infusion/aspiration (I/A) cleanup after tissue phacoemulsification in which fine remnants of the tissue are aspirated at a lower rate and through a smaller opening than the open end, comprising:

a tube adapted to be joined to the distal end of the work tip without being in fixed relation to the housing or work tip of the surgical hand piece, said tube being sized so that it slides over the distal end of the work tip, and defines at least one aspiration hole with a diameter larger than the diameter of the lateral hole of the work tip and located toward the distal end of the tube, and when the distal end of the tube is at a first distance $L^1$ from the distal end of the work tip, aspiration during phacoemulsification occurs through the aspiration hole of the tube and the open end of the work tip, and when the distal end of the tube is at a second and smaller distance $L_2$ from the open end of the work tip during I/A cleanup, aspiration through the open end of the work tip is blocked by the tube and aspiration occurs through the aspiration hole of the tube and the lateral hole in the work tip.

2. The adapter of claim 1 wherein the tube further includes lateral irrigation openings located farther from the distal end than the aspiration hole, said irrigation openings being adapted to discharge irrigation fluid located within the tube to a surgical site.

3. The adapter of claim 2 wherein the hand piece further includes a sleeve surrounding at least in part the single lumen work tip and forming an irrigation channel between the work tip and the sleeve, and wherein the tube is sized to fit over a distal end of the sleeve so that irrigation fluid in the irrigation channel reaches the irrigation openings in the tube, and the sleeve is made, at least in part, of silicone material.

4. The adapter of claim 1 wherein the aspiration hole is in the form of a plurality of openings.

5. The adapter of claim 1 wherein the tissue emulsification is phacoemulsification of a cataract in an eye of a patient and the cleanup is performed on lens epithelial cells in the capsular bag of the eye of the patient.

6. The adapter of claim 2 wherein the work tip has a cross section over most of its length and an expanded cross section portion at its distal end, sleeve of said adapter having a cross section such that it can slide over the expanded cross section portion of the work tip; and whereby irrigation fluid can be accommodated in a space between the work tip proximally of the expanded cross section portion of the work tip and an interior surface of the tube and can exit the tube at said irrigation openings.

7. The adapter of claim 1 wherein the tube is adapted to be moved along the work tip from $L_1$ to $L_2$ or vice versa, so as to change the aspiration flow.

8. The adapter of claim 2 wherein the sleeve lateral irrigation openings discharge continuous irrigation fluid regardless of whether the tube is at $L_1$ or $L_2$.

9. A surgical hand piece comprising:

a housing for a source of ultrasonic vibration;

a single lumen work tip fastened to the handpiece and adapted to be ultrasonically vibrated thereby so as to perform tissue emulsification, said work tip having an open end and a lateral hole through it with a diameter smaller than the diameter of the open end and located at a distance in the proximal direction from the open end;

an adapter designed to convert the work tip to perform infusion/aspiration (I/A) cleanup after tissue emulsification, said adapter comprising a tube adapted to be slid over the distal end of work tip without being in fixed relation to the work tip of the hand piece, said tube defining at least one aspiration hole with a diameter larger than the diameter of the lateral hole of the work tip and located toward the distal end of the tube; and wherein, when the distal end of the tube is at a first distance $L_1$ from the distal end of the work tip, aspiration occurs through the aspiration hole of the tube and the open end of the work tip, and when the distal end of the tube is at a second and smaller distance $L_2$ from the open end of the work tip, aspiration through the open end of the work tip is blocked by the tube and aspiration occurs through the aspiration hole of the sleeve and the lateral hole in the work tip.

10. A plurality of adapters according to claim 4 wherein the plurality of openings of the aspiration hole of one of the adapters is in a different pattern than the plurality of openings of another of the adapters.

11. A plurality of adapters according to claim 4 wherein the plurality of openings of the aspiration hole of one of the adapters have a different size than another of the adapters.

12. A plurality of adapters according to claim 4 wherein the plurality of openings of the aspiration hole of one of the adapters have a different shape than another of the adapters.

* * * * *